(12) United States Patent
Li

(10) Patent No.: US 9,277,192 B2
(45) Date of Patent: Mar. 1, 2016

(54) MONITORING SYSTEM OF REAL TIME IMAGE CONTROL FOR RADIOPHARMACEUTICAL AUTOMATIC SYNTHESIZING APPARATUS IN A MICRO HOT CELL

(71) Applicant: Ming-Hsin Li, Taoyuan County (TW)

(72) Inventor: Ming-Hsin Li, Taoyuan County (TW)

(73) Assignee: INSTITUTE of NUCLEAR ENERGY RESEARCH, Jiaan Village, Longtan, Taoyuan (TW)

( * ) Notice: Subject to any disclaimer, the term of this patent is extended or adjusted under 35 U.S.C. 154(b) by 504 days.

(21) Appl. No.: 14/049,228

(22) Filed: Oct. 9, 2013

(65) Prior Publication Data

US 2015/0097943 A1 Apr. 9, 2015

(51) Int. Cl.
*H04N 7/18* (2006.01)
*G01N 23/00* (2006.01)
*G01N 21/84* (2006.01)

(52) U.S. Cl.
CPC ............... *H04N 7/188* (2013.01); *G01N 21/84* (2013.01); *G01N 23/00* (2013.01)

(58) Field of Classification Search
CPC ....... H04N 7/188; G01N 23/00; G01N 21/84; G01T 1/00
USPC ................................................. 348/82, 83, 86
See application file for complete search history.

(56) References Cited

U.S. PATENT DOCUMENTS

| | | | | |
|---|---|---|---|---|
| 4,526,311 A | * | 7/1985 | Schröder | 228/119 |
| 4,727,179 A | * | 2/1988 | Schmalfuss | 348/83 |
| 4,876,593 A | * | 10/1989 | Bauer et al. | 348/83 |
| 6,339,372 B1 | * | 1/2002 | Warnock et al. | 340/531 |
| 7,391,028 B1 | * | 6/2008 | Rubenstein | 250/370.08 |
| 2003/0093430 A1 | * | 5/2003 | Mottur | 707/10 |
| 2004/0163118 A1 | * | 8/2004 | Mottur | 725/105 |
| 2008/0084473 A1 | * | 4/2008 | Romanowich | 348/135 |
| 2011/0063447 A1 | * | 3/2011 | Vilim et al. | 348/159 |
| 2012/0224046 A1 | * | 9/2012 | Waugh | 348/82 |
| 2012/0327228 A1 | * | 12/2012 | Nomura | 348/143 |
| 2014/0224964 A1 | * | 8/2014 | Solomon et al. | 250/208.1 |

FOREIGN PATENT DOCUMENTS

| | | | |
|---|---|---|---|
| EP | 419971 A2 | * | 4/1991 |
| JP | 59138996 A | * | 8/1984 |
| JP | 2005130401 A | * | 5/2005 |
| KR | 100807337 B1 | * | 2/2008 |

OTHER PUBLICATIONS

"GE Power—Hot Cell Surveillance"; Dec. 2012; <http://www.ge-mcs.com/microsites/power/NSS-PTZ04-0105.html>.*

* cited by examiner

*Primary Examiner* — John Villecco

(57) ABSTRACT

The present invention relates to a system of real time micro hot cell image control for radiopharmaceutical automatic synthesizing apparatus including at least one CCD camera, a plurality of radioactivity detector, a logic control device, a computer interface control device. The plurality of radioactivity detector are connected to the logic control device, and the logic control device sends a corresponding location code to the computer interface control device when the detected radioactivity value is greater than the threshold value for selecting a nearest CCD camera and sending the taken image of the location to the computer interface control device for monitoring whether the automatic production line of radiopharmaceuticals is kept in normal operation.

5 Claims, 4 Drawing Sheets

MONITORING SYSTEM OF REAL TIME IMAGE CONTROL FOR RADIOPHARMACEUTICAL AUTOMATIC SYNTHESIZING APPARATUS IN A MICRO HOT CELL

BACKGROUND OF THE INVENTION

1. Field of the Invention

The present invention relates to a monitoring system of real time image control, and in particular to a monitoring system of real time image control for radiopharmaceutical automatic synthesizing apparatus operating in a micro hot cell for determining whether the radioactivity value is greater than the threshold value and displaying the location of the component of the radiopharmaceutical automatic synthesizing apparatus with an alert when the radioactivity value being detected is greater than the threshold value.

2. Description of Related Art

The radiopharmaceutical automatic synthesizing apparatus associated with a nuclide generator for radiolabeling is an important technology nowadays. The prior art has revealed that it is insufficient for its design, disposition, and arrangement of hardware and needs to be improved. The monitoring system of automatic synthesizing apparatus operating in a micro hot cell disclosed in periodicals, such as Adamovics et al. 2013, Farfan et al. 2012, Chen et al. 2010, Wooten et al. 2005, Villadsen et al. 2002, and Hoover et al. 1999, Rahman et al. 2012, showed that faults occurred during the production of radiopharmaceutical in a micro hot cell are difficult to be identified and resolved with appropriate treatment immediately.

US Patent Publication No. 20120113245 discloses a device for observing the inside of a micro hot cell and a method for maintaining the device thereof; nevertheless, the cited document did not mention a method of using said device in combination with radiopharmaceutical automatic synthesizing apparatus for the purpose of radiopharmaceutical yield improvement.

A traditional device for monitoring automatic synthesizing apparatus displays only the radioactivity of important units of automatic synthesizing apparatus or the overall appearance images of automatic synthesizing apparatus thus cannot help find out the source of problems such as the synthesizing apparatus crashes or fluid pipelines shedding that needs an immediately troubleshooting with appropriate treatment to ensure smooth production.

SUMMARY OF THE INVENTION

The primary object of the present invention is to provide a security monitoring system of real time image control for a production line of radiopharmaceutical automatic synthesizing apparatus, which contains at least one charge coupled device camera (hereinafter referred to as CCD camera) installed in a micro hot cell providing real time image function with Positron Emission Tomography (PET) pharmaceutical automatic synthesizing apparatus. With features of a logic control device and a computer interface control device of the present invention, when a component of the radiopharmaceutical automatic synthesizing apparatus exhibits higher radioactivity value, the site of the production line can be zoomed and filmed by the CCD cameras with real time images for displaying on a computer monitor with an alert.

Another object of the present invention is to provide a security monitoring system for a production line of radiopharmaceutical automatic synthesizing apparatus to monitor the site of the production line operating in a micro hot cell for manufacturing PET pharmaceuticals, such as Gallium-68-DOTA or Rehnium-188-Liposome, or Single-Photon Emission Computed Tomography (SPECT) pharmaceuticals. The radionuclide like Gallium-68 or Rehnium-188 is a core element of pharmaceutical labeling process. When the radiopharmaceutical automatic synthesizing apparatus starting the pharmaceutical labeling process, the radionuclide, such as Gallium-68, Fluorine-18, Lutetium-177, or Rehnium-188, flows in the production line through each component of the radiopharmaceutical automatic synthesizing apparatus containing a plurality of material vials, a plurality of reagent vials, a waste vial, a chromatography column, a plurality of solenoid valves, a collection vials, and a plurality of pipelines. The CCD cameras are used to monitor each component of the radiopharmaceutical automatic synthesizing apparatus in a normal operation, prevent the automatic synthesizing apparatus from crashing or the reaction fluid pipelines from shedding, provide a criterion for determining whether the automatic synthesizing apparatus is in a normal operation condition, and take appropriate treatment promptly when required without reducing the yield of radiopharmaceuticals.

Still another object of the present invention is to provide a logic control device, including a radioactivity value comparator, a code identification circuit, and a CCD camera selector. After receiving the data from radioactivity detector, the radioactivity value comparator is activated to determine whether the detected value is greater than the threshold value preset in the radioactivity value comparator. If the detected value is greater than the threshold value, the radioactivity value comparator will issue a command to the code identification circuit to obtain a corresponding location code of the radioactivity detector. The CCD camera selector receives the decoded location code from the code identification circuit and activates the CCD camera that corresponds to the location of the component which exhibited higher radioactivity than threshold value detected by the radioactivity detector. The images of the site of high radioactivity area taken by the CCD camera are zoomed and displayed on the computer monitor for locating a fault position.

In order to accomplish the above objects, a monitoring system of real time image control of the present invention is provided for production lines of radiopharmaceutical automatic synthesizing apparatus in a micro hot cell, comprising: a plurality of CCD cameras, a plurality of radioactivity detectors located inside a micro hot cell; a logic control device, and a computer interface control device located outside the micro hot cell, wherein the logic control device is connected to the computer interface control device and a plurality of CCD cameras. The data of the radioactivity detected by the radioactivity detectors are sent to the computer interface control device through the logic control device for displaying on the computer monitor.

When the detected radioactivity value is greater than the threshold value, a location code of the radioactivity detector that indicated greater radioactivity value is sent to the logic control device from the computer interface control device for decoding. The logic control device based on the decoded location code selects the CCD camera that is in proximity to the location of the radioactivity detector, which has detected the greater radioactivity value, for taking images of the site of greater radioactivity area and sending the images to the computer interface control device to display on the computer monitor with an alert.

According to the device described above, wherein the logic control device comprises a code identification circuit, a radioactivity value comparator, and a CCD camera selector;

wherein the radioactivity value comparator is connected to a plurality of radioactivity detector and a computer interface control device; wherein the code identification circuit is connected to the computer interface control device and the CCD camera selector; wherein the CCD camera selector is connected to at least one CCD camera.

According to the device described above wherein the CCD camera is sheltered by hemispheric cover for protecting CCD camera from radioactivity contamination.

According to the monitoring system of the present invention described above, the detected radioactivity value of the components are shown on the computer monitor by descending order, and the detected value greater than the threshold value is shown in flash.

The above and other objects, features and advantages of the present invention will become apparent from the following detailed description taken with the accompanying drawings.

DETAILED DESCRIPTION OF THE PREFERRED EMBODIMENT

Figure 1:
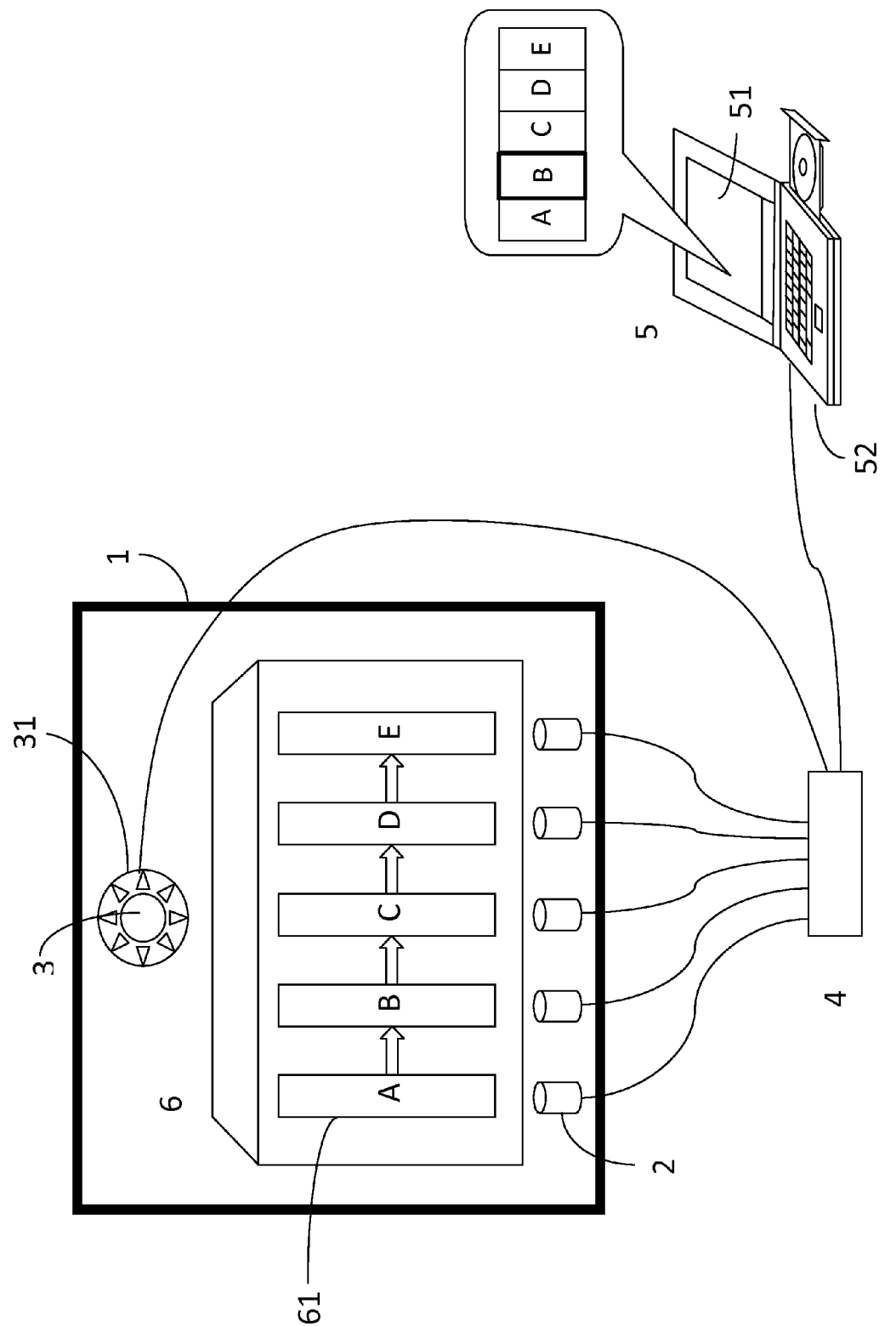
FIG. 1 is a perspective view of a monitoring system of real time image control for radiopharmaceutical automatic synthesizing apparatus in a micro hot cell of the present invention.

With reference to FIG. 1, a monitoring system of real time image control for radiopharmaceutical automatic synthesizing apparatus 6 in a micro hot cell 1 of the present invention comprises a plurality of CCD cameras 3 located inside the micro hot cell for monitoring the production line; a plurality of radioactivity detectors 2 located inside the micro hot cell 1 for detecting radioactivity; a logic control device 4 for determining radioactivity with threshold value and selecting a CCD camera for taking images of area where radioactivity value is greater than the threshold value; and a computer interface control device 5 for monitoring and displaying the images taken by the plurality of CCD cameras 3; wherein the radioactivity detectors 2 are connected to the computer interface control device 5 through the logic control device 4, and the logic control device 4 is connected to at least one CCD camera 3.

In an embodiment, the components 61A and 61B of the radiopharmaceutical automatic synthesizing apparatus 6 are set as one group, and the components 61C, 61D, and 61E are set as the other group. The radioactivity detector 2 sends the detected radioactivity values of the components 61A to 61E to the computer interface control device 5 through the logic control device 4. When the radioactivity value of the component 61B is determined to be greater than the threshold value, the computer interface control device 5 sends the encoded location code of the radioactivity detector 2 to the logic control device 4 for decoding and obtaining a corresponding location code of the radioactivity detector 2. A CCD camera 3 is selected based on the decoded location code for taking real time image of the component 61B and sends to the computer interface control device 4. The image taken by the CCD camera 3 can be zoomed and displayed on the computer monitor 51 with an alert 52.

In an embodiment, the plurality of CCD cameras 3 is sheltered by hemispheric cover 31 for protecting CCD cameras 3 from radioactivity contamination.

Figure 2:
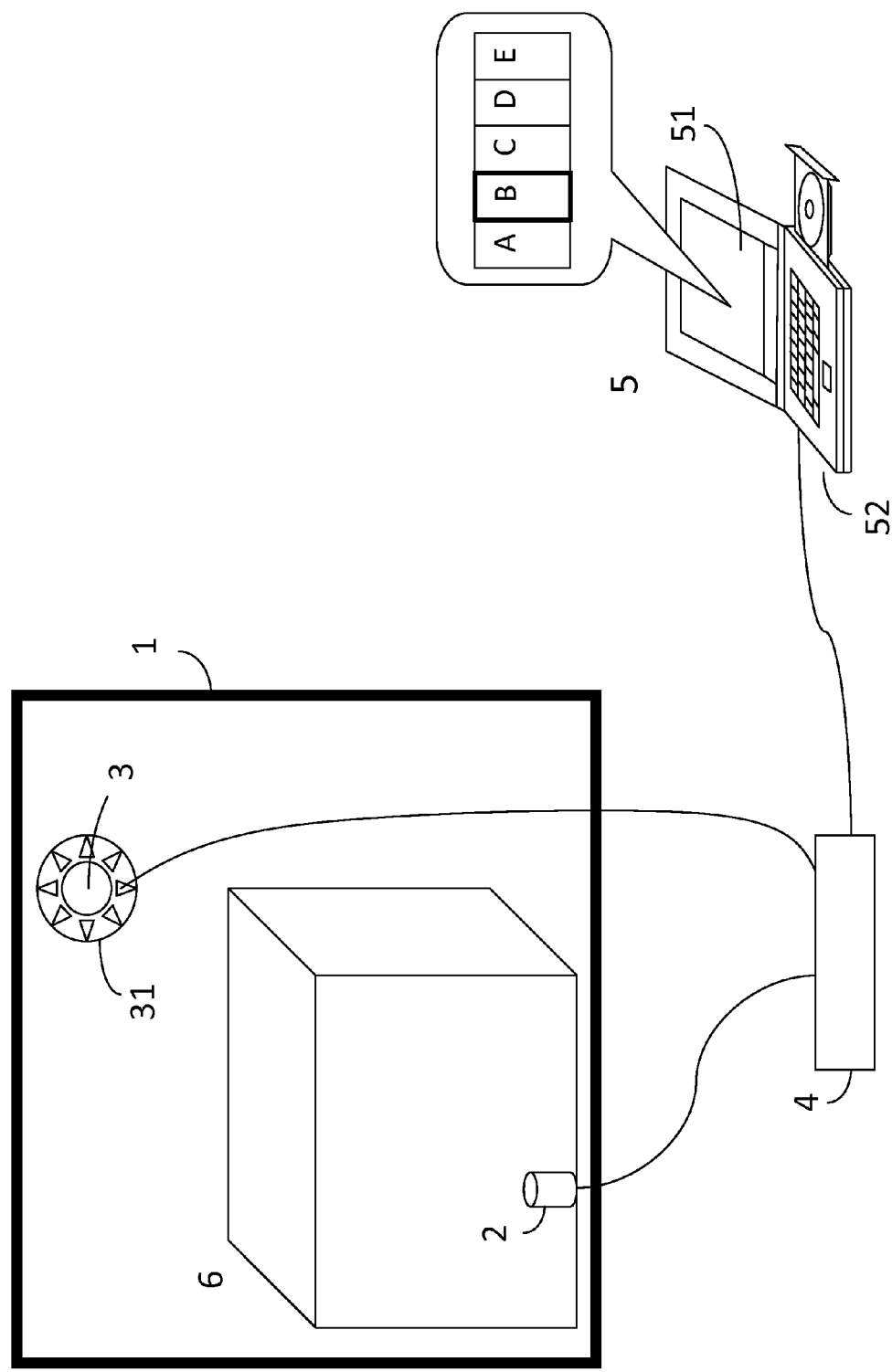
FIG. 2 is a rear view of the monitoring system of real time image control for radiopharmaceutical automatic synthesizing apparatus in a micro hot cell of the present invention.

With reference to FIG. 2, a rear view of the device for real time image control for radiopharmaceutical automatic synthesizing apparatus 6 in a micro hot cell 1 shows that the radioactivity detectors 2 are provided surrounding the radiopharmaceutical automatic synthesizing apparatus 6 for providing a complete radioactivity detection area without blind spot.

Figure 3:
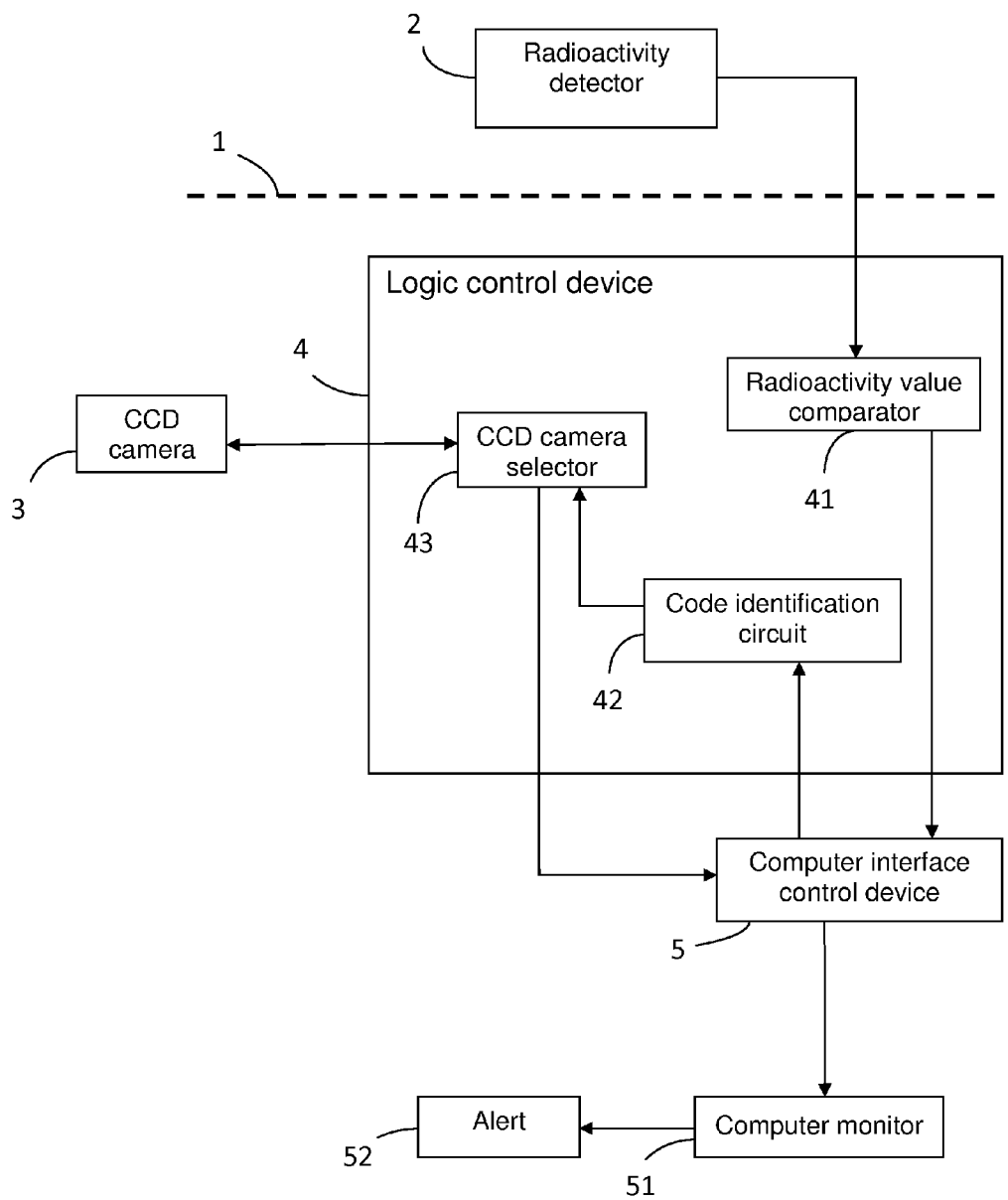
FIG. 3 is an exemplary block diagram illustrating the interior of the logic control device of the present invention.

With reference to FIG. 3, an exemplary block diagram illustrating the interior of the logic control device 4. The logic control device 4 comprises a radioactivity value comparator 41, a code identification circuit 42, and a CCD camera selector 43; wherein the radioactivity value comparator 41 is connected to a plurality of radioactivity detectors 2 for comparing the detected radioactivity values with a threshold value, and to the computer interface control device 5 to provide the detected radioactivity values and comparing results for displaying on the computer monitor 51; the code identification circuit 42 is connected to the computer interface control device 5 for receiving an encoded location code of the radioactivity detector 2 which has detected a radioactivity value greater than a threshold value, and to the CCD camera selector 43 for selecting a CCD camera 3; and the CCD camera selector 43 is connected to a plurality of CCD cameras 3 for selection of CCD camera 3 when a location code provided by the code identification circuit 42 is received.

Figure 4:
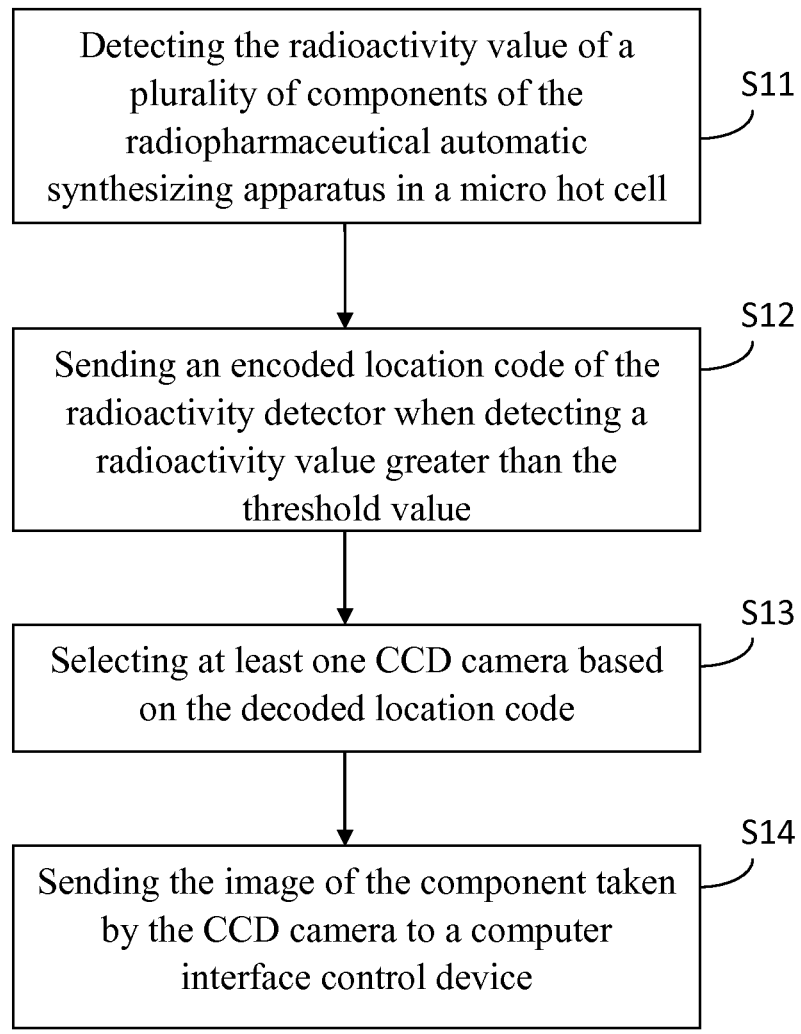
FIG. 4 is a flow chart of the monitoring system of real time image control for radiopharmaceutical automatic synthesizing apparatus in a micro hot cell of the present invention.

With reference to FIG. 4, a method of real time image control for a production line of radiopharmaceutical automatic synthesizing apparatus in a micro hot cell 1 comprises steps of:

S11: detecting the radioactivity value of a plurality of components 61 of the radiopharmaceutical automatic synthesizing apparatus 6 with a plurality of radioactivity detectors 2 and sending detected radioactivity values to a computer interface control device 5 through a logic control device 4 for displaying on a computer monitor 51, and determining whether the radioactivity values are greater than the threshold value by a radioactivity value comparator 41 provided in the logic control device 4;

S12: sending an encoded location code of the radioactivity detector 2 from the computer interface control device 5 to the code identification circuit 42 when detecting a radioactivity value greater than the threshold value for decoding and obtaining the decoded location code of the radioactivity detector 2;

S13: selecting at least one CCD camera 3 by the CCD camera selector 43 based on the decoded location code sent from the code identification circuit 42; and S14: sending images of the component 61 taken by the CCD camera 3 to the computer interface control device 5 for displaying or zooming on the computer monitor 51 with an alert 52.

The foregoing invention has been described in detail by way of illustration and example for purposes of clarity and understanding. It will be apparent to those of ordinary skill in the art that variations, changes, modifications and alterations may be applied to the compositions and/or monitoring system described herein without departing from the true spirit, concept and scope of the invention.

What is claimed is:

1. A monitoring system of real time image control for a production line of radiopharmaceutical automatic synthesizing apparatus in a micro hot cell, comprising: at least one CCD camera inside the micro hot cell for monitoring the production line, a plurality of radioactivity detectors located inside the micro hot cell for detecting radioactivity, a logic control device located outside the micro hot cell for determining a radioactivity threshold value and selecting a CCD camera for taking images of area where radioactivity value is being detected greater than the threshold value, and a computer interface control device located outside the micro hot cell for monitoring and displaying the images taken by the selected CCD camera; wherein the radioactivity detectors are connected to the computer interface control device through the logic control device, and the logic control device is connected to at least one CCD camera.

2. The monitoring system of claim 1, wherein the logic control device comprises a code identification circuit, a radioactivity value comparator, and a CCD camera selector;

wherein the radioactivity value comparator is connected to the plurality of radioactivity detectors for comparing the radioactivity values with a threshold value, and to the computer interface control device to provide a comparing result of the radioactivity values being detected for displaying on the computer monitor;

wherein the code identification circuit is connected to the computer interface control device for receiving the encoded location code of the radioactivity detector which has detected a radioactivity value greater than a threshold value, and to the CCD camera selector for selecting a CCD camera; and wherein the CCD camera selector is connected to a plurality of CCD cameras for selection of CCD camera when a location code provided by the code identification circuit is received.

3. A method of real time image control for a production line of radiopharmaceutical automatic synthesizing apparatus in a micro hot cell, comprising steps of:

detecting the radioactivity value of a plurality of components of the radiopharmaceutical automatic synthesizing apparatus with a plurality of radioactivity detectors and sending the detected radioactivity values to a computer interface control device through a logic control device for displaying on a computer monitor, and determining whether the radioactivity value is greater than a threshold value by a radioactivity value comparator provided in the logic control device;

sending an encoded location code of the radioactivity detector when detecting a radioactivity value greater than the threshold value from the computer interface control device to the code identification circuit for decoding and obtaining the location code of the radioactivity detector;

selecting at least one CCD camera by the CCD camera selector based on the decoded location code of the radioactivity detector; and sending the image of the component taken by the selected CCD camera with greater radioactivity value than the threshold value to the computer interface control device for displaying or zooming on the computer monitor with an alert.

4. The method of claim 3, wherein the radioactivity values detected are displayed on the computer monitor in order by value, and the detected radioactivity value that is greater than the threshold value is displayed in flash.

5. The method of claim 3, the CCD camera is selected according to the decoded location code received from the code identification circuit.

* * * * *